(12) United States Patent
Pawlus

(10) Patent No.: US 6,884,072 B2
(45) Date of Patent: Apr. 26, 2005

(54) REFRACTORY DIE WITH PIN FOR TEETH RESTORATION AND METHOD

(76) Inventor: John G. Pawlus, 7730 Mill Run, Columbus, IN (US) 47201

(*) Notice: Subject to any disclaimer, the term of this patent is extended or adjusted under 35 U.S.C. 154(b) by 43 days.

(21) Appl. No.: 10/339,037

(22) Filed: Jan. 9, 2003

(65) Prior Publication Data

US 2004/0137401 A1 Jul. 15, 2004

(51) Int. Cl.[7] ............ A61C 11/00; A61C 19/00
(52) U.S. Cl. ............ 433/213; 433/34; 433/74
(58) Field of Search ............ 433/34, 74, 213, 433/223

(56) References Cited

U.S. PATENT DOCUMENTS

| | | | | |
|---|---|---|---|---|
| 4,661,071 A | * | 4/1987 | Bell et al. | 433/223 |
| 4,721,464 A | * | 1/1988 | Roden et al. | 433/74 |
| 4,793,806 A | * | 12/1988 | Elledge | 433/74 |
| 4,917,347 A | * | 4/1990 | Fenick | 249/54 |
| 5,788,490 A | * | 8/1998 | Huffman | 433/74 |

OTHER PUBLICATIONS

Paul Sturridge and Irfan Ahmad.; CERAMICS; QDT 1999; Preparation and Fabrication of Ceramic Veneerlay Restorations pp 169–177.

* cited by examiner

Primary Examiner—Cary E. O'Connor
(74) Attorney, Agent, or Firm—Woodard, Emhardt, Moriarty, McNett & Henry LLP

(57) ABSTRACT

A refractory die removably mountable to a base with a model die for use in producing a crown or veneer to be attached to a tooth to be restored. The model die, produced from die stone, is removably mounted to the base with a portion of the model die corresponding to the tooth to be restored being separable therefrom and used to produce the refractory die. Porcelain is placed on the refractory die to produce the crown or veneer.

13 Claims, 6 Drawing Sheets

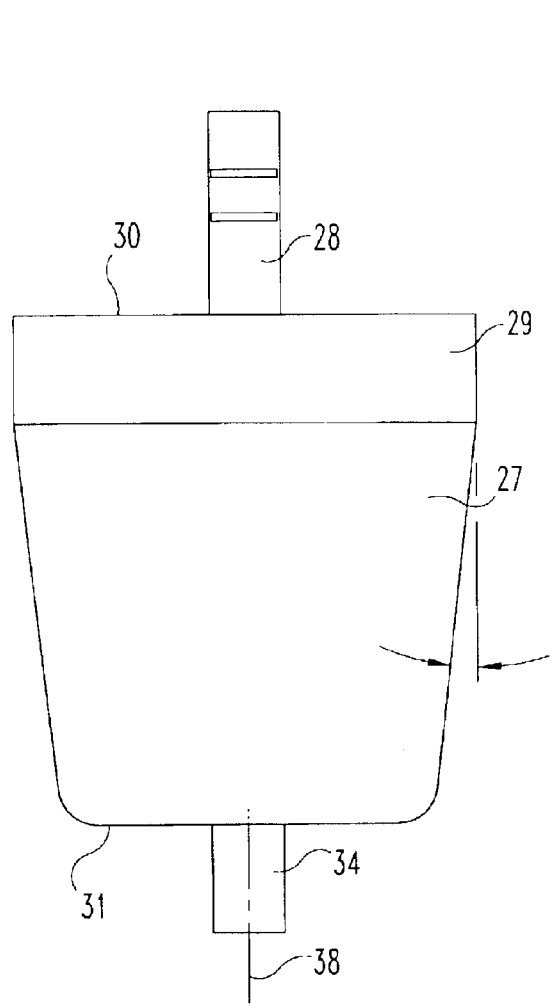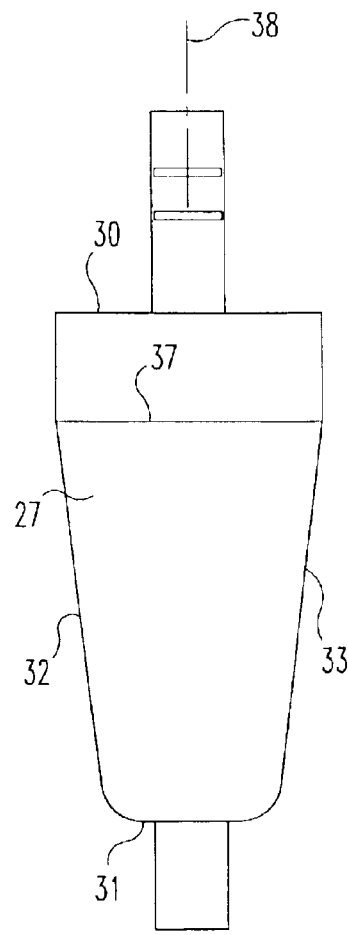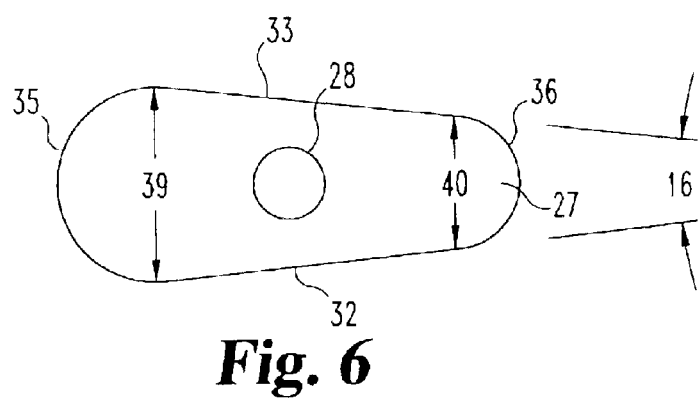

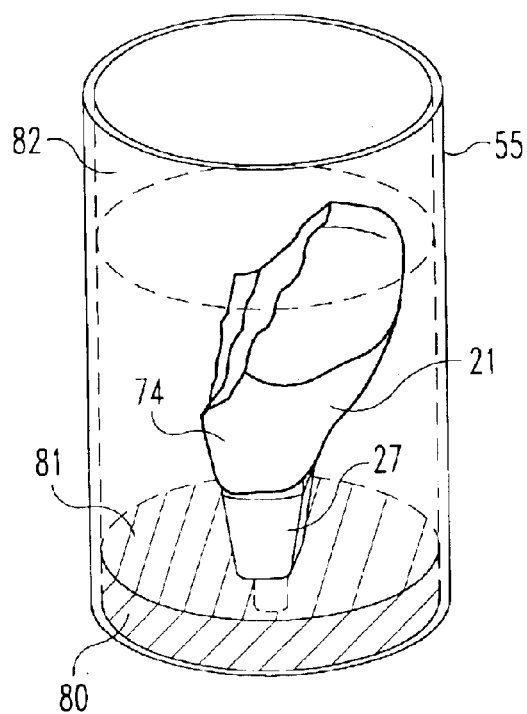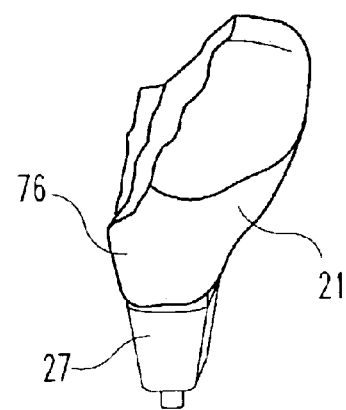
Fig. 9  Fig. 10
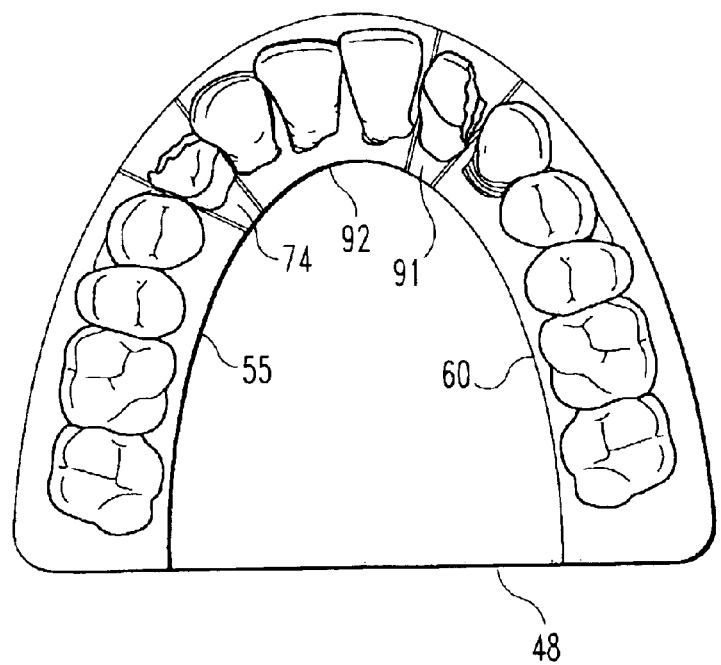
Fig. 11

REFRACTORY DIE WITH PIN FOR TEETH RESTORATION AND METHOD

BACKGROUND OF THE INVENTION

The present invention relates generally to the field of teeth restoration and more particularly to the use of refractory dies.

DESCRIPTION OF THE PRIOR ART

In order to add a veneer or a crown to a damaged tooth, the dentist makes a single impression of the entire set of teeth including the damaged tooth. For example, if the damaged tooth is an upper tooth then a yieldable material such as plastic, rubber and the like is used to make an impression of the entire upper set of teeth including the damaged tooth. As discussed in "Preparation and Fabrication of Ceramic Veneerley" by Paul Sturridge and Irfan Ahmad in QDT, Quintessence of Dental Technology, Volume 22, page 169 (1999), a working cast is then prepared from the impression. Typically, the working cast will be produced by pouring die stone into the impression and then allowing the die stone to harden. Small cylindrical pins are then mounted to the bottom of the working cast to enable the working cast to be mounted to a base and to allow for individual removable dies to be repositioned correctly in the base. The dies are subsequently sectioned, trimmed and repositioned back on the base. An impression of this trimmed model in the base is taken with silicon impression material and the base is removed with the individual dies retained in the impression. The dies corresponding to any teeth that are to be restored utilizing refractory dies are then removed from the impression and these voids are then filled with refractory material. A special refractory pin is placed in each die and a new base is poured.

An alternate prior art method used to create a working model with refractory dies is to trim the dies that will be used to make the refractory dies and to then reposition the dies back into the original impression. The remaining portion of the model is then poured up in dental stone. The individual dies are subsequently removed and duplicated in silicone. The dies are removed from the silicone impression and refractory material is poured into the impression to produce the refractory dies. The resulting product is then placed into the working model.

The first method requires the additional step of pouring of a second base. Further, the method has the disadvantage of having to redo the entire model should an individual die be damaged. The second method introduces possible positioning error by having to be replaced in the original impression. The second method also requires increased time to prepare the individual dies prior to duplicating.

The refractory die includes a pair of small pins extending outwardly in the same direction as the remaining cylindrical pins extending from the working cast. When the refractory die along with the working cast is within the mold, a plaster base is poured resulting in a final cast mounted to a base.

A further problem with the prior art methods is the breakage of refractory material surrounding the small cylindrical pins that project from the portion of the refractory die representing the tooth to be restored. Disclosed herein is a new large pin used in combination with the portion of the model die representing the tooth to be restored to produce a refractory die with a refractory pin extending therefrom with an enlarged external body.

SUMMARY OF THE INVENTION

One embodiment of the present invention is a method of restoring a first tooth within a set of teeth comprising the first step of creating a first impression of a set of teeth with the tooth to be restored. A model die is created from the impression with the model die having a first portion corresponding to the tooth to be restored. The first portion is provided with a mounting pin having an enlarged section that is then mounted to a base. Next, the model die is removed from the base and severed into multiple portions including at least the first portion with the enlarged section projecting therefrom and a second portion. A second impression of the first portion with the enlarged section is produced allowing creation of a first refractory die providing a replica of the tooth and the enlarged section projecting therefrom. The refractory die and the second portion are mounted onto the base by inserting the pins and the replica of the enlarged section into the base. Replacement material is then applied to the refractory die to allow for the final configuration of the tooth to be restored.

Another embodiment of the present invention is a combination for use in producing a crown or veneer for a damaged tooth within a set of teeth comprising, a base and a multi-part model die of a set of teeth removably mounted to the base. The model die includes a damaged tooth portion separable from the model die corresponding to the damaged tooth within the set of teeth. The portion is removably mounted independently of the remaining part of the model die to the base. A pin is mounted to the portion of the model die with the pin having an enlarged section extending outwardly from the portion and into the base. A refractory die is created and replaces the portion with the pin. The refractory die is used to create the crown for the damaged tooth.

It is an object of the present invention to provide a new and improved method for restoring teeth.

A further object of the present invention is to provide a mold of a set of teeth including a refractory die of a tooth to be restored removably mounted to a base with separable portions to allow replacement of any one portion without the necessity of reproducing the entire model.

A further object of the present invention is to provide a mounting pin to removably mount a refractory die within a model die set of teeth.

Related objects and advantages of the present invention will be apparent from the following description.

BRIEF DESCRIPTION OF THE DRAWINGS

FIG. 4 is front view of a refractory die-mounting pin.

FIG. 5 is a side view of the pin of FIG. 4.

FIG. 6 is a top view of the pin of FIG. 4.

FIG. 9 is a perspective view of the model die portion removed from FIG. 8 positioned within a container to produce an impression.

FIG. 10 is a perspective view of a refractory die of the tooth to be restored.

FIG. 11 is the same view as FIG. 8 only showing a model die corresponding to multiple teeth to be restored.

DESCRIPTION OF THE PREFERRED EMBODIMENTS

Figure 1:
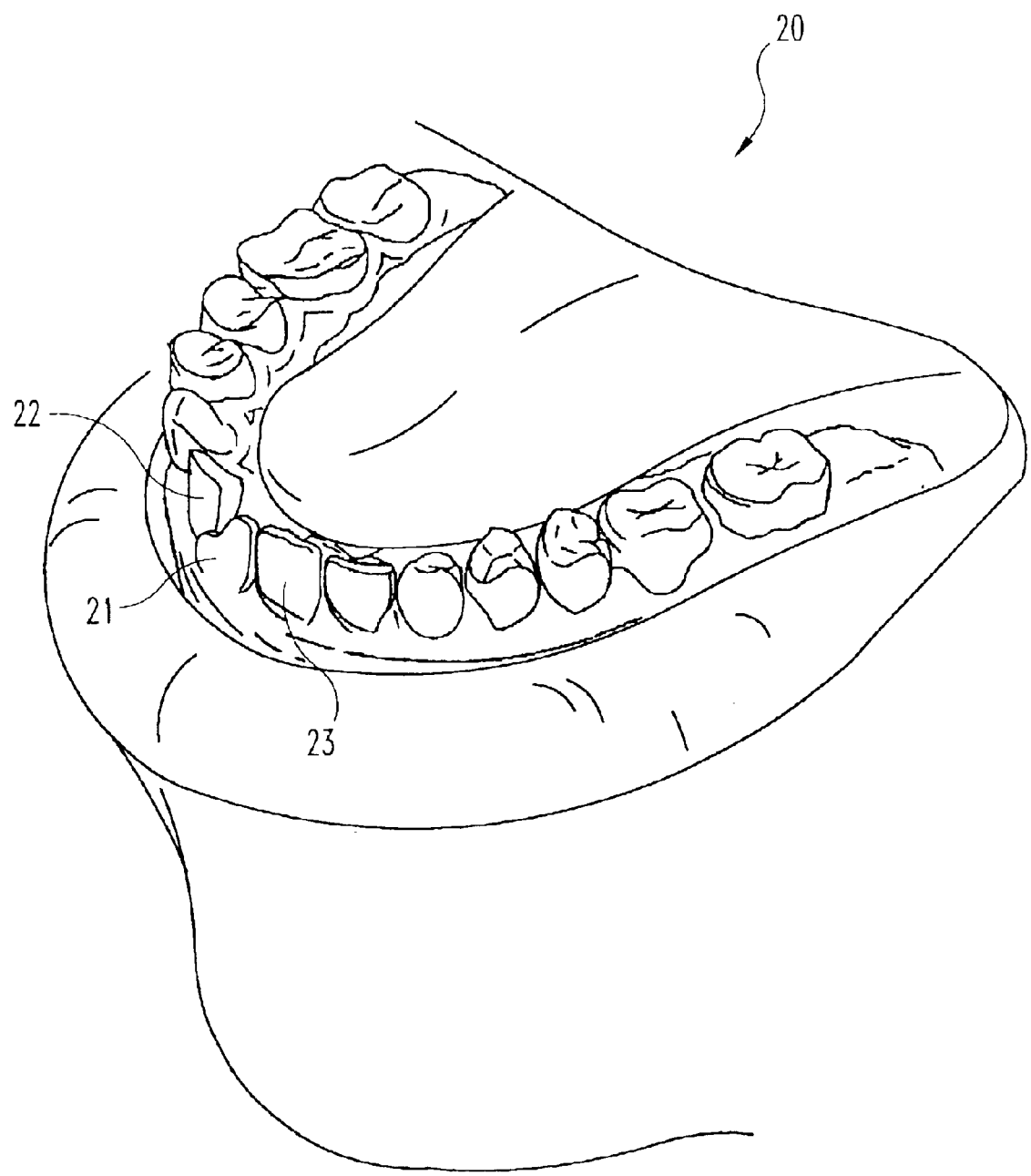
FIG. 1 is a perspective view of a grouping or arch of teeth including a tooth to be restored.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown an arch of teeth 20 positioned within a person's mouth and illustrating a front tooth 21 to be restored positioned between and adjacent teeth 22 and 23. In order to restore tooth 21, either porcelain or other suitable material may be used to build up the tooth to a final configuration.

Figure 2:
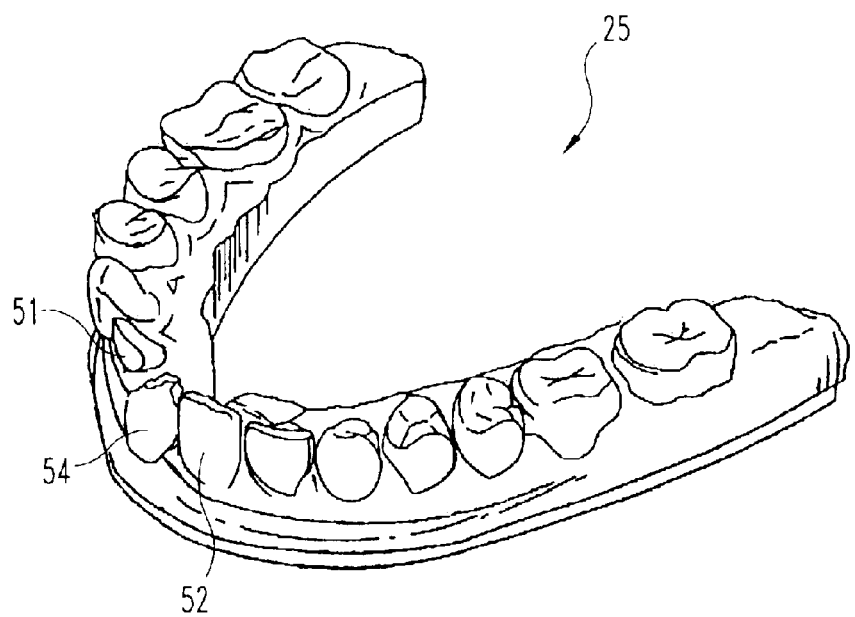
FIG. 2 is a perspective view of a model die replica of the teeth of FIG. 1.

Prior to pouring an impression of teeth 20, the tooth 21 to be restored is prepared by removing decay, old fillings, etc. In the preferred embodiment, a conventional impression is then produced of teeth 20 by pouring impression material, such as polyvinyl siloxane into a mold or tray and placing the tray into the mouth allowing the impression to set up. The tray is then removed with the impression material having in it cavities corresponding to the teeth and providing a female die. The model die is then prepared by pouring a mixture of material into the impression. A conventional mixture includes for example, 20 ml of water along with 100 grams of die stone which is a gypsum with a resin. The mixture is stirred under a vacuum to eliminate air bubbles. The mixture is hardened producing a male model replica 25 (FIG. 2). Die model 25 is trimmed and the bottom is ground to produce a flat even surface.

Figure 3:
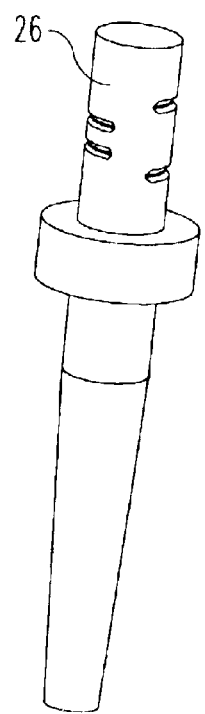
FIG. 3 is a perspective view of a cylindrical pin used to mount portions of the model die of FIG. 2 to a base.

Two different types of mounting pins are mounted to the bottom of replica 25. The pins include conventional cylindrical pins 26 (FIG. 3) and a unique refractory die pin 27 (FIGS. 4–6). Holes are drilled in the bottom surface of replica 25 with pins 26 and the cylindrical top end 28 of pin 27 then being inserted into the cylindrical holes. A standard glue, such as cyanoacrylate is first placed into the holes to securely hold the pins therein.

Pin 27 has a main body 29 with a top end 30, a bottom end 31, a pair of opposite side surfaces 32 and 33, a front surface 35 and rear surface 36. A pair of cylindrical pins 28 and 34 project outwardly respectively from top end 30 and bottom end 31 of main body 29. The main body is tapered both in a horizontal direction and a vertical direction as viewed in FIGS. 4 and 5. That is, surfaces 32 and 33 diverge as the surfaces extend from bottom end 31 to intermediate area 37 located between ends 30 and 31. Likewise, surfaces 35 and 36 diverge as they extend upwardly from bottom end 31 to an intermediate area 37 located between ends 30 and 31. Surfaces 32 and 33 extend vertically from area 37 to top end 30 along lines parallel to longitudinal axis 38 extending centrally through the pin. Front surface 35 and rear surface 36 are rounded being convex and cooperatively with side surfaces 32 and 33 providing a larger width 39 at the front end of the pin as compared to the width 40 at the rear of the pin. Surfaces 32 and 33 extend convergingly toward end 36 forming an included angle 16. The rounded front surface 35 and rounded rear surface 36 extend vertically along lines parallel to axis 38 between area 37 and top end 30. Main body portion 29 has an oblong horizontal cross-section from end 30 to end 31.

Figure 7:
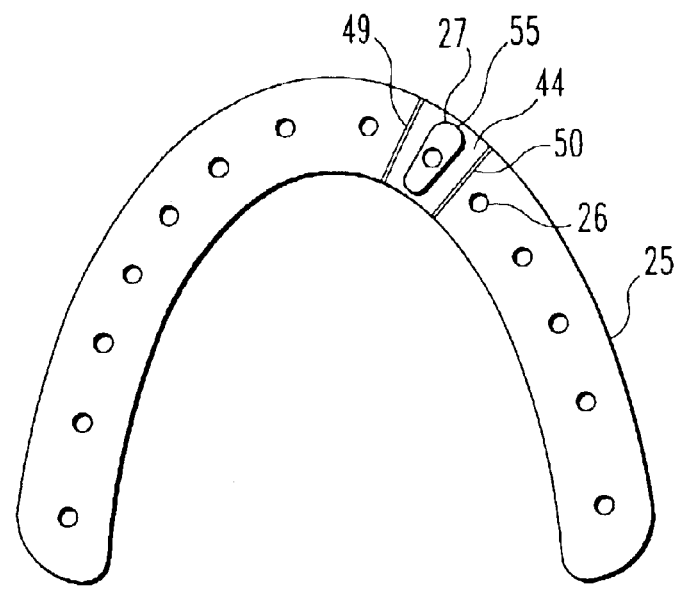
FIG. 7 is a bottom view of the die of FIG. 2 with the pins of FIGS. 3 and 4 mounted thereto.
Figure 12:
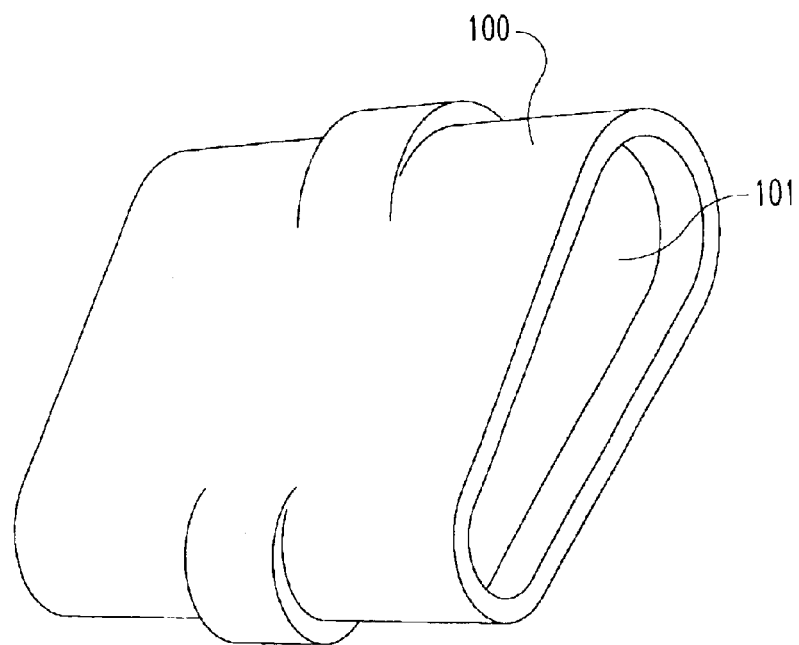
FIG. 12 is a perspective view of a sleeve for mounting to the pin of FIG. 4.
Figure 13:
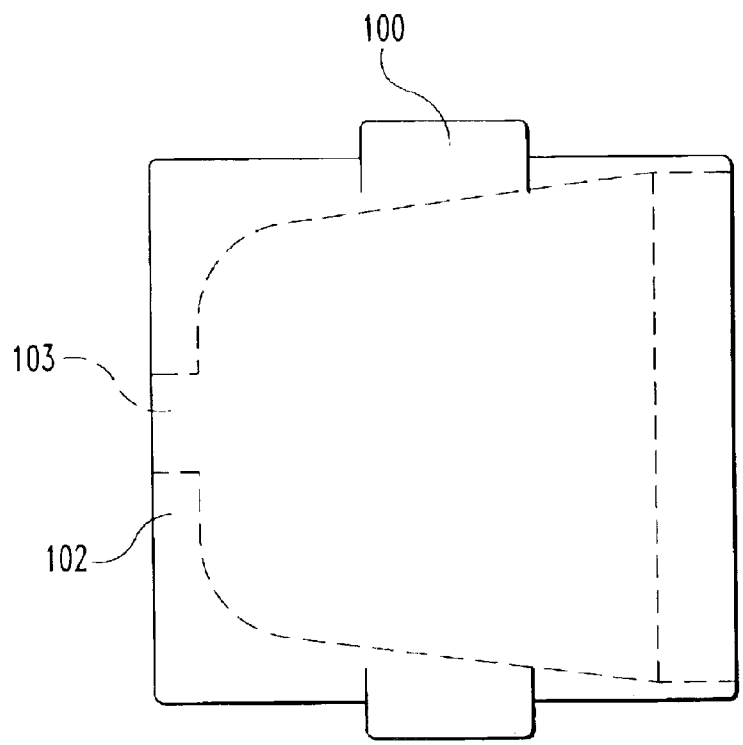
FIG. 13 is a side view of the sleeve of FIG. 12.

The cylindrical pins 26 (FIG. 3) are inserted into the holes previously drilled in the bottom of model 25 (FIG. 7) with the exception of the portion 44 of the model upon which is formed the tooth 21 to be restored. Instead of mounting pins 26 to portion 44, the refractory die pin 27 is mounted by inserting cylindrical top end 28 into a cylindrical hole drilled in the bottom of portion 44 thereby positioning the enlarged main body 29 beneath the model. For a relatively small sized tooth, such as, a front tooth, the rear surface 36 of pin 27 is located aft of the tooth to be restored whereas the front surface 35 faces outwardly and in a forward direction from the row of teeth. Once the adhesive within the pinholes has set up, plastic sleeves are installed on pins 26 and pin 27 in order to keep a base from sticking onto the pins. Commercially available sleeves are mounted to pins 26 whereas a special new sleeve 100 (FIGS. 12 & 13) is mounted to pin 27. Sleeve 100 has a hollow interior 101 to receive the main body of pin 27. The bottom wall 102 of the sleeve is closed. Hole 103 extends through wall 102 enabling end 34 of the pin to extend through the wall. Likewise, a stone separator is painted onto the bottom of model 25 to keep the model from sticking to the plaster base. Commercially available stone separators are available, such as an acrylic liquid.

The plaster base is produced by pouring a plaster liquid mix into a mold. For example, 100 grams of plaster with 23 ml of water may be poured into a mold and mixed under a vacuum. Die model 25 is then inserted into the mold with the model teeth facing upwardly. Once the plaster has hardened, the model with plaster base is removed from the mold. A plaster base 48 (FIG. 8) is therefore provided with a plurality of upwardly opening pinholes formed therein that receive the downwardly extending pins of model 25.

Figure 8:
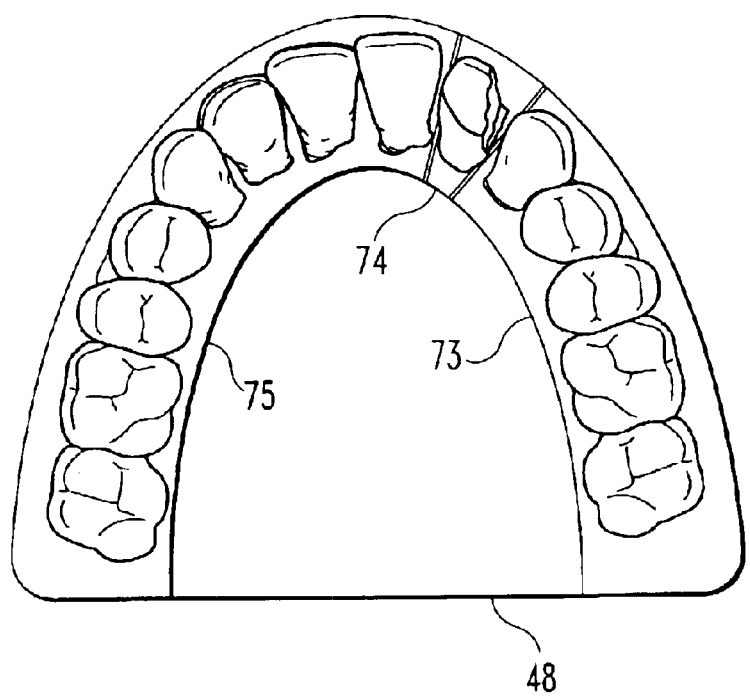
FIG. 8 is a top view of the model die of FIG. 7 mounted to a base with the portion of the model die representing the tooth to be restored removable therefrom.

Model 25 is then removed from base 48 with portion 44 then being cut from the model by sawing along dashed lines 49 and 50. Line 49 (FIG. 7) extends between model tooth 54 (FIG. 2) corresponding to the tooth 21 (FIG. 1) and adjacent model tooth 51 corresponding to tooth 22 whereas line 50 extends between model tooth 54 and adjacent model tooth 52. Model die is therefore broken into a portion 73, a middle portion 74 corresponding to the tooth 21 to be restored, and a portion 75 (FIG. 8). The poured base encloses pins 26 and pin 27 including the enlarged main body 29 and bottom pin 34.

Die model portion 74 (FIG. 9) consisting of the portion of the model representing the tooth 21 to be restored along with a pin 27 is inserted into container 55 subsequently filled with a liquid soft silicone with the tooth facing upwardly. Container 55 has a removable base 80 with a soft top surface 81 through which pin end 34 may be inserted to mount pin 27 to the removable base. Shell 82 is removably mounted to base 81 and encloses portion 74. The silicone is poured into shell 81 covering portion 74. Once the soft silicone has set up, base 81 is removed from shell 82 and portion 74 is removed forming a female hole or mold of portion 74. A release agent is sprayed into the hole and refractory material is poured into the hole formed within container 55. The refractory material has a co-efficient of thermal expansion approximately equal to porcelain subsequently applied thereto. Thus, the refractory material can be heated to a high temperature in order to fuse the porcelain without the refractory material breaking. Once the refractory material has set for an hour, the resulting replica 76 (FIG. 10)

consisting of a replica of model portion 74 may be removed from container 55 and mounted to base 48 in place of portion 74.

Base 48 and refractory die 76 are fired to an initial temperature of, for example, of approximately 700 degrees centigrade and then inserted into a porcelain oven, for example, at 1000 degrees centigrade for five minutes in the conventional manner. Once the refractory die 76 has cooled, the porcelain may be stacked on die 76 or a veneer is added, configured, and fired in a high temperature oven to the final tooth configuration in the conventional manner. The resulting crown may then be removed and mounted in the patient's mouth.

Several advantages result from utilizing a model die consisting of the die stone portions 73 and 75 whereas the tooth to be restored consists of a refractory die 76. An advantage is in the event the die 76 breaks during the heat application and porcelain addition, then a new refractory die can be produced by repeating the procedure of pouring a new refractory die in container 55 utilizing the hole formed by portion 74 without the need of producing new die stone portions 73 and 75 along with base 48. Further, in the event it is desired to have better access to the sides of refractory die 76 when mounted to the base, portions 73 and 75 may be removed during the porcelain addition. Most importantly, the present invention does not require either the model die to be re-inserted into the mold when the refractory die is poured or the taking of a second impression of the entire model die since the refractory die is poured by itself. In addition, only a single base 48 is poured in the present invention unlike the prior methods.

In many cases, multiple teeth are to be restored within the same set of teeth with the teeth to be restored not being located in adjacent fashion. The teeth to be restored may correspond to the positions occupied by die portions 74 and 91 mounted to base 48 in FIG. 11. Portions 91 and 74 are separated by die stone portion 92. Individual refractory dies may be produced from portions 91 and 74 in a manner identical to the production of refractory die 76. In the event the refractory die breaks corresponding to portion 91 whereas the refractory is successfully produced corresponding to portion 74, then the process must be repeated only for the refractory die corresponding to portion 91 thereby providing exceptional savings in both cost and time. Both portions 74 and 91 include a pin 27.

The method of producing a crown or veneer for attachment to tooth to be restored includes the first step of creating a first impression of the set of teeth. A model die of die stone material is then created from the first impression. A portion of the model die is severed that corresponds to the tooth to be restored. The severed portion of the model die is used to make a further impression that is used to produce the refractory die. The refractory die and the remaining portion of the model die is removably mounted to a base. Cylindrical pins mount the model die to the base and a pin with an enlarged section mounts to the base the portion of the model die corresponding to the tooth to be restored. Porcelain is then formed and fired on the refractory die and subsequently attached to the tooth to be restored.

When mounting the pin with an enlarged section for a small tooth, the enlarged section is positioned so that its enlarged front portion faces outwardly and forwardly with respect to the set of teeth. In the event that a second tooth is to be restored that is within the set, then the method described herein is repeated for the second tooth.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method of producing replacement material to restore a first tooth within a set of teeth comprising the steps of:
   creating a first impression of a set of teeth with a first tooth;
   creating from said impression a model die of said set of teeth with said model die having a first portion corresponding to said first tooth to be restored;
   providing mounting pins;
   providing a pin with an enlarged section;
   mounting said mounting pins to said model die;
   mounting said pin with enlarged section to said first portion so said enlarged section projects therefrom;
   creating a base adjacent said model die enclosing said pins and said enlarged section of said pin;
   removing said model die with said pins and said pin with enlarged section from said base;
   severing said model die into multiple portions including at least said first portion with said enlarged section projecting therefrom and a second portion;
   creating a second impression of said first portion with said enlarged section projecting therefrom;
   creating a first refractory die from said second impression providing a replica from refractory material of said tooth and said enlarged section projecting therefrom;
   mounting said refractory die and said second portion onto said base by inserting said pins and said replica of said tooth and enlarged section into said base; and,
   placing material onto said refractory die to enable said first tooth to be restored.

2. The method of claim 1 and further comprising the step of:
   severing said model die so said multiple portions includes a third portion with said first portion being located between said second portion and said third portion, and said pins are mounted to and project from said second portion and said third portion.

3. The method of claim 1 wherein said set of teeth are arranged in a curve and said enlarged section has a thick part and further comprising the step of:
   orienting said enlarged section on said first portion so said thick part faces outwardly from said curve.

4. The method of claim 1 wherein said set of teeth includes a second tooth to be restored that is spaced apart from said first tooth by teeth from said set and further comprising the steps of:
   said first impression and said model die are created of said set of teeth with said first tooth and said second tooth, said model die having a third portion corresponding to said second tooth and said second portion corresponding to teeth of said set between said first tooth and said second tooth;
   providing an additional pin with an enlarged section and mounting said additional pin to said third portion so said enlarged section of said additional pin projects therefrom;
   said base is created so it also encloses said enlarged section of said additional pin;
   severing said model die into multiple portions including said third portion with said additional pin with enlarged section projecting therefrom;

creating a third impression of said third portion with said additional pin with enlarged section projecting therefrom;

creating a second refractory die from said third impression providing a replica of said second tooth and enlarged section projecting therefrom;

mounting said first refractory die, said second refractory die, and said second portion onto said base; and, placing material onto said second refractory die to finally configure said second tooth.

5. The method of claim 4 and comprising the additional steps of:

discarding one of said multiple portions in the event of damage thereto while retaining any remaining undamaged portions.

6. A pin for mounting a refractory tooth die comprising:

a main body including a top end, a bottom end, a front and a back, said main body being cylindrical at said top end and having a middle portion between said top end and said bottom end, said middle portion being tapered and having a pair of opposite sides extending from said back to said front which diverge as said sides extend from said back to said front, said front being rounded as it extends between said opposite sides; and:

said opposite sides diverge as said sides extend from said bottom end toward said top end, said front and back diverge as said front and back extend from said bottom end toward said top end;

said main body includes a longitudinal axis and said middle portion includes an upper portion whereat said opposite sides extend parallel to said axis, said front and back only diverge between said bottom end and said upper portion, said back is rounded as it extends between said opposite sides and said bottom end is cylindrical.

7. A combination for use in producing a crown or veneer for a damaged tooth within a set of teeth comprising:

a base;

a multi part model die of a set of teeth removably mounted to said base, said model die including a damaged tooth portion separable from said model die and corresponding to a damaged tooth within said set of teeth, said portion removably mounted independently of said model die to said base;

a pin mounted to said portion of said model die with said pin having an enlarged section extending outwardly from said portion and into said base; and, a refractory die removably mounted independently from said model die to said base, said refractory die replicating and replacing said portion with said pin.

8. The combination of claim 7 and further comprising:

material placeable upon said refractory die for firing and producing a crown or veneer for a damaged tooth.

9. The combination of claim 7 wherein:

said refractory die and said model die are separable although mounted to said base to allow independent replacement of either in the event of damage to either.

10. The combination of claim 7 wherein:

said multi part model die includes a first portion and a second portion separable from said model die independently of each other with said damaged tooth portion locatable therebetween until replaced by said refractory die which is then locatable between said first portion and said second portion when mounted to said base.

11. The combination of claim 7 wherein:

said pin includes a main body including a top end, a bottom end, a front and a back, said main body having a middle portion between said top end and said bottom end, said middle portion being tapered and having a pair of opposite sides extending from said back to said front which diverge as said sides extend from said back to said front.

12. The combination of claim 11 wherein:

said front is rounded as it extends between said opposite sides and said opposite sides diverge as said sides extend from said bottom end toward said top end, said front and back diverge as said front and back extend from said bottom end toward said top end, said top end and said bottom end are cylindrical whereas said middle portion has an oblong cross section.

13. The combination of claim 12 wherein:

said front is mounted to said base facing outwardly and in a forward direction relative to said set of teeth.

* * * * *